(12) United States Patent
Bodner et al.

(10) Patent No.: US 9,848,816 B1
(45) Date of Patent: Dec. 26, 2017

(54) SYSTEM AND METHOD FOR CORTICAL ENTRAINMENT

(71) Applicant: MIND Research Institute, Irvine, CA (US)

(72) Inventors: Mark Bodner, Irvine, CA (US); Andrew Coulson, Irvine, CA (US); Theodore Smith, Irvine, CA (US)

(73) Assignee: MIND Research Institute, Irvine, CA (US)

( * ) Notice: Subject to any disclaimer, the term of this patent is extended or adjusted under 35 U.S.C. 154(b) by 918 days.

(21) Appl. No.: 14/098,847

(22) Filed: Dec. 6, 2013

Related U.S. Application Data

(60) Provisional application No. 61/734,889, filed on Dec. 7, 2012.

(51) Int. Cl.
*A61B 5/0476* (2006.01)
*A61B 5/00* (2006.01)
*A61B 5/0488* (2006.01)
*A61B 5/0484* (2006.01)

(52) U.S. Cl.
CPC .......... *A61B 5/4094* (2013.01); *A61B 5/0484* (2013.01)

(58) Field of Classification Search
CPC ... A61B 5/4094; A61B 5/0476; A61B 5/7275; A61B 5/04012; A61B 5/7282
See application file for complete search history.

(56) References Cited

U.S. PATENT DOCUMENTS

2005/0197590 A1* 9/2005 Osorio .................. A61B 5/048
600/544

* cited by examiner

*Primary Examiner* — Christine H Matthews
*Assistant Examiner* — Joshua D Lannu
(74) *Attorney, Agent, or Firm* — Klein, O'Neill & Singh, LLP

(57) ABSTRACT

Cortical entrainment device (CED) and associated methods are provided. The CED device includes an electroencephalographic (EEG) analysis module configured to receive and process an EEG waveform for analyzing brain activity of a patient with epilepsy or a seizure disorder; an interictal epileptiform discharge (IED) analysis module configured to receive and process an IED waveform for analyzing the brain activity of the patient; and a diagnostic module that is configured to interface with the EEG analysis module and the IED analysis module, to evaluate spectral and temporal waveform characteristics, and to provide instructions to a therapy module for providing a stimulus for the patient based on the analysis by the EEG analysis module and the IED analysis module.

8 Claims, 15 Drawing Sheets

| Functional Configuration | Packaging Alternatives |
|---|---|
| A | Rack mount or stand-alone device, signal processing software or card |
| B | Rack mount or stand-alone device (portable or stationary), or hearing aid |
| C | Rack mount or stand-alone device, or home-based bedside unit |
| D | Rack mount or stand-alone device |

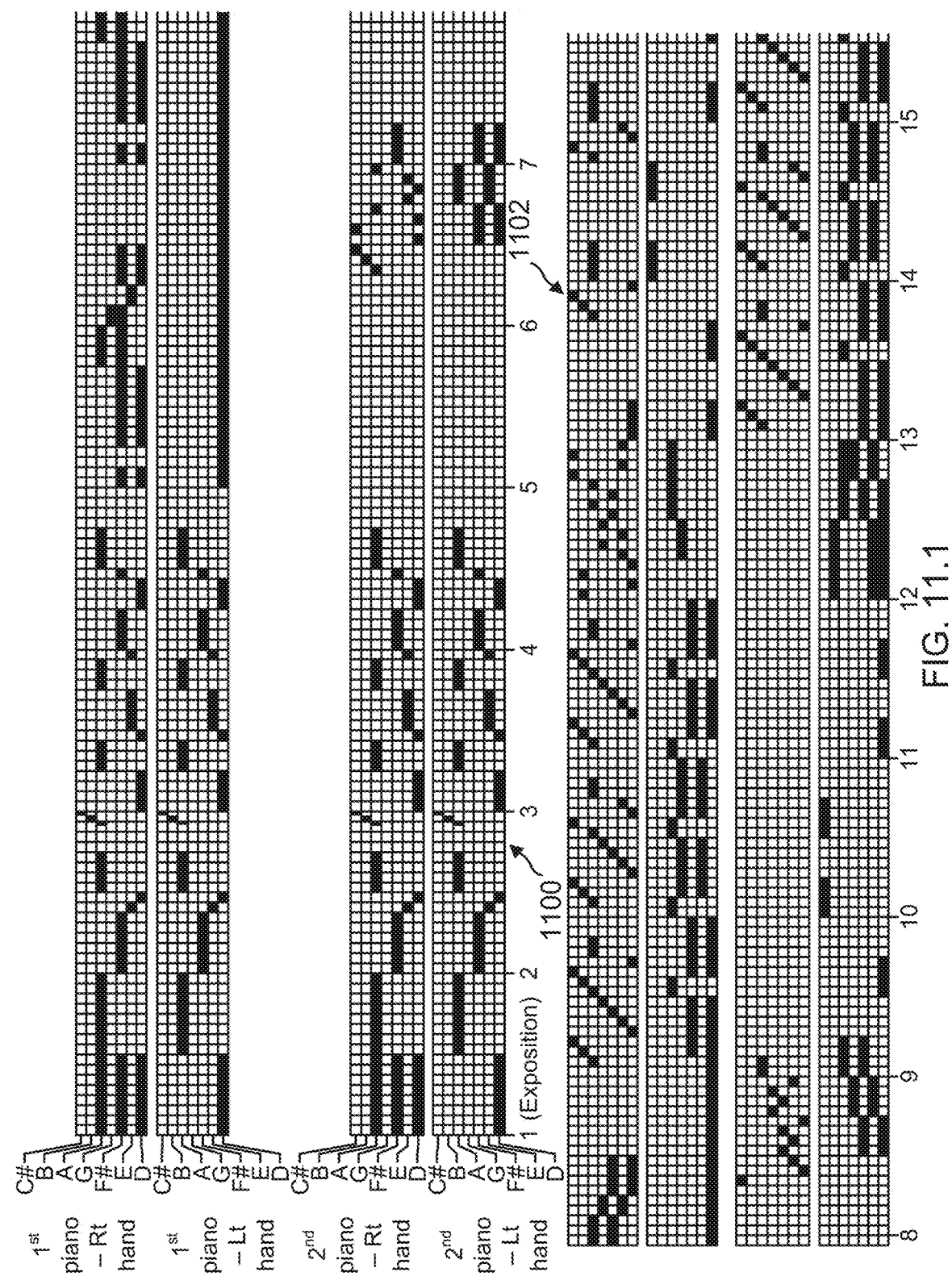
FIG. 11.1

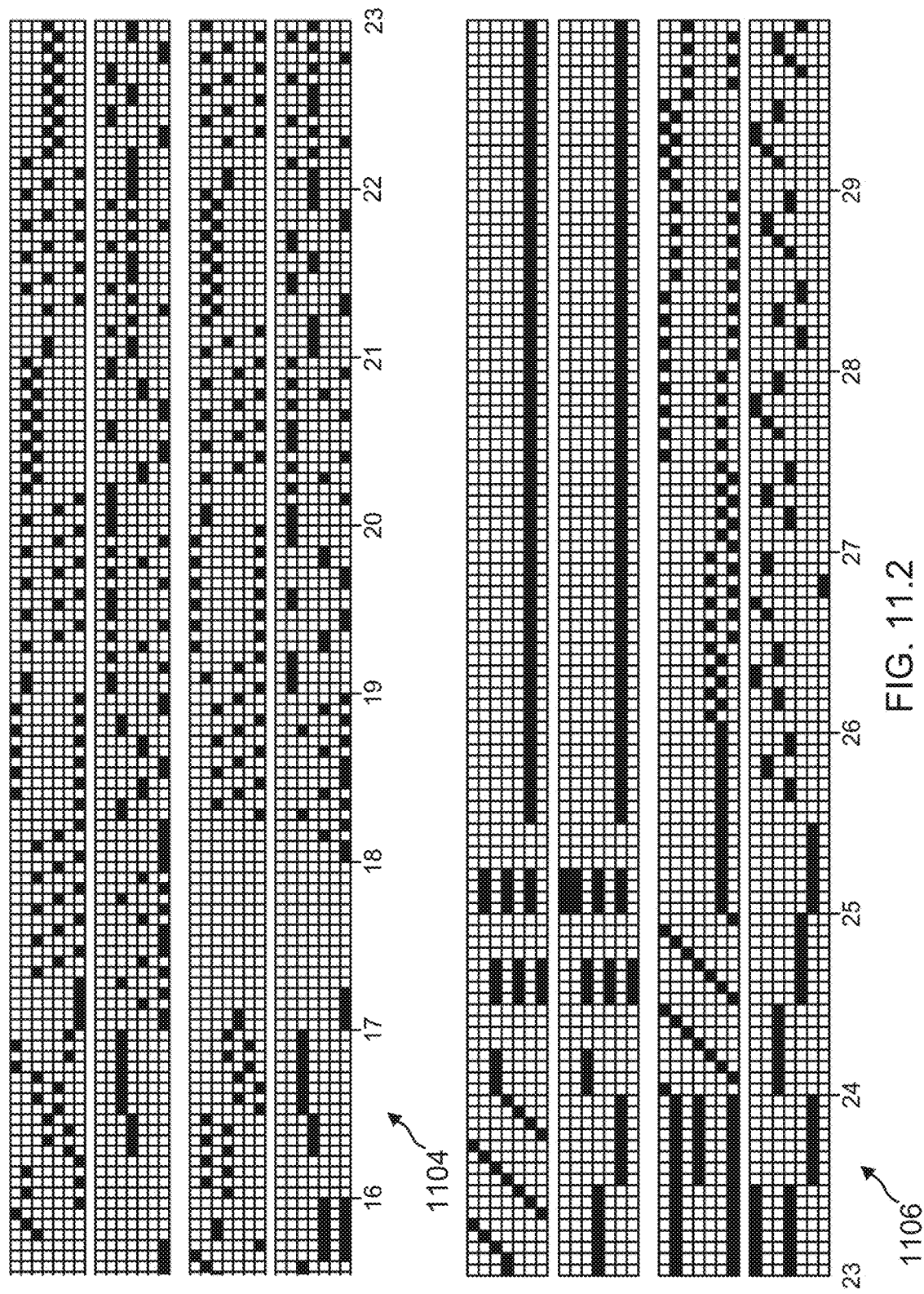
FIG. 11.2

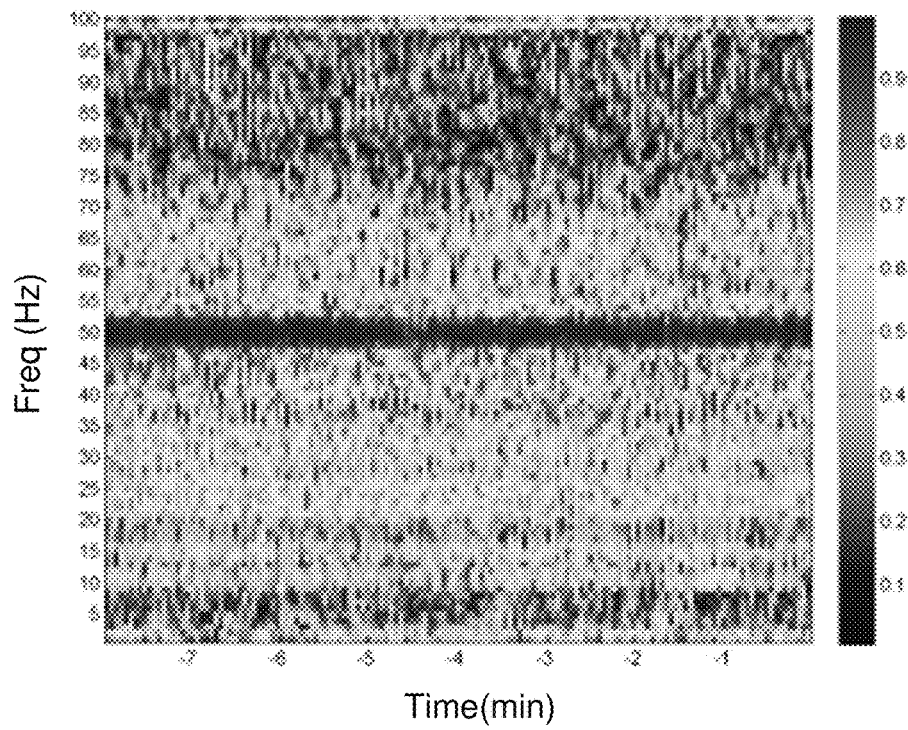
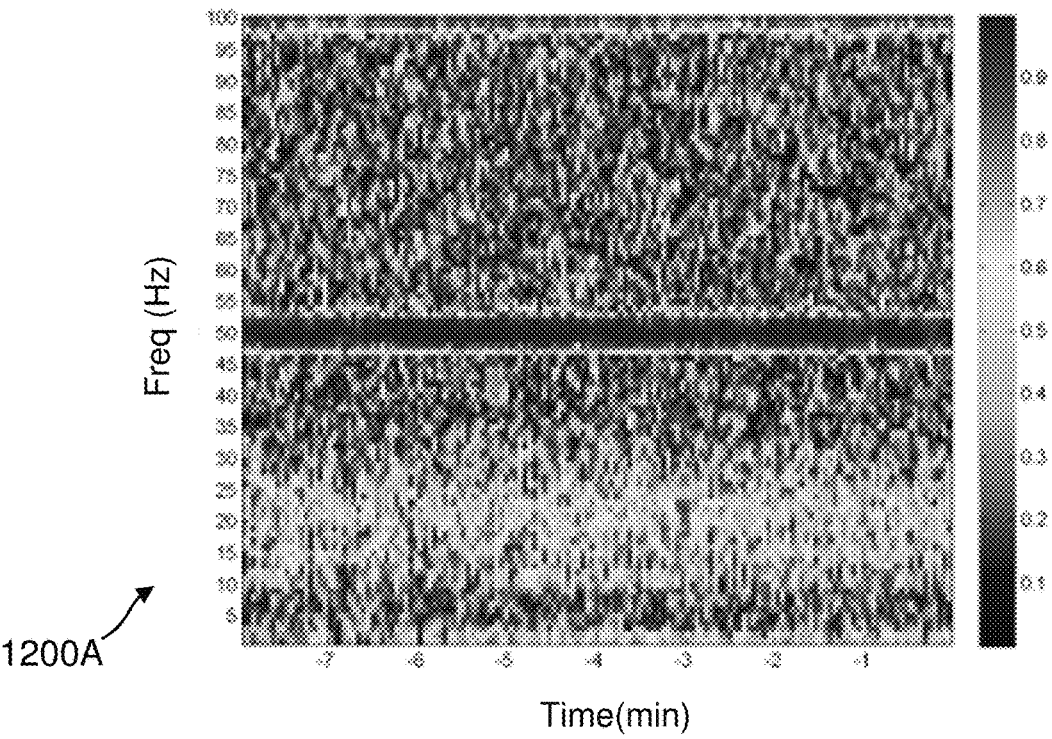
1200A
FIG. 12A

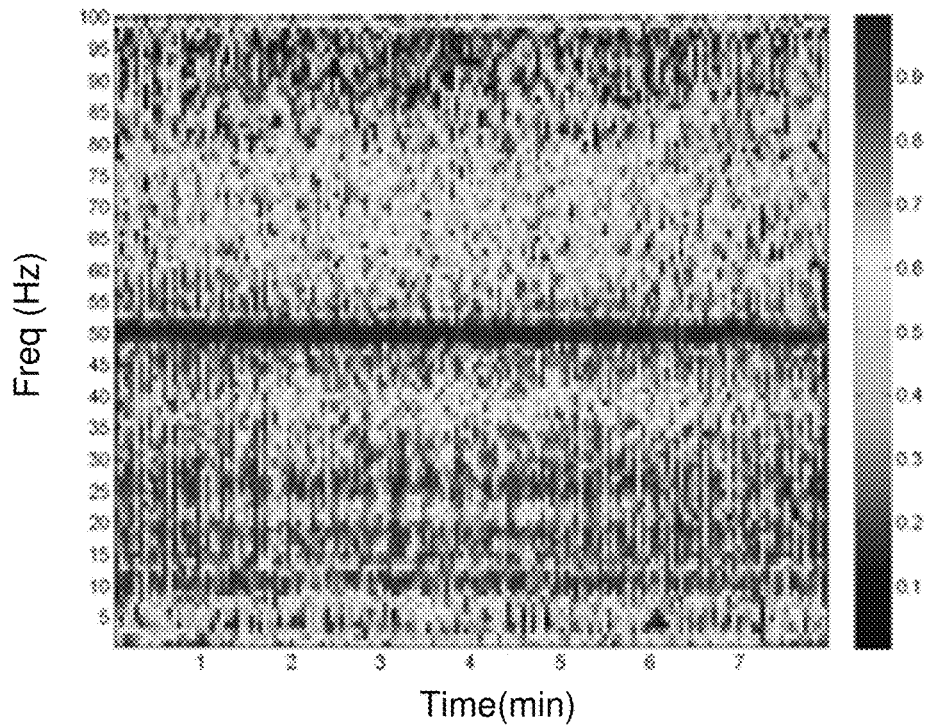
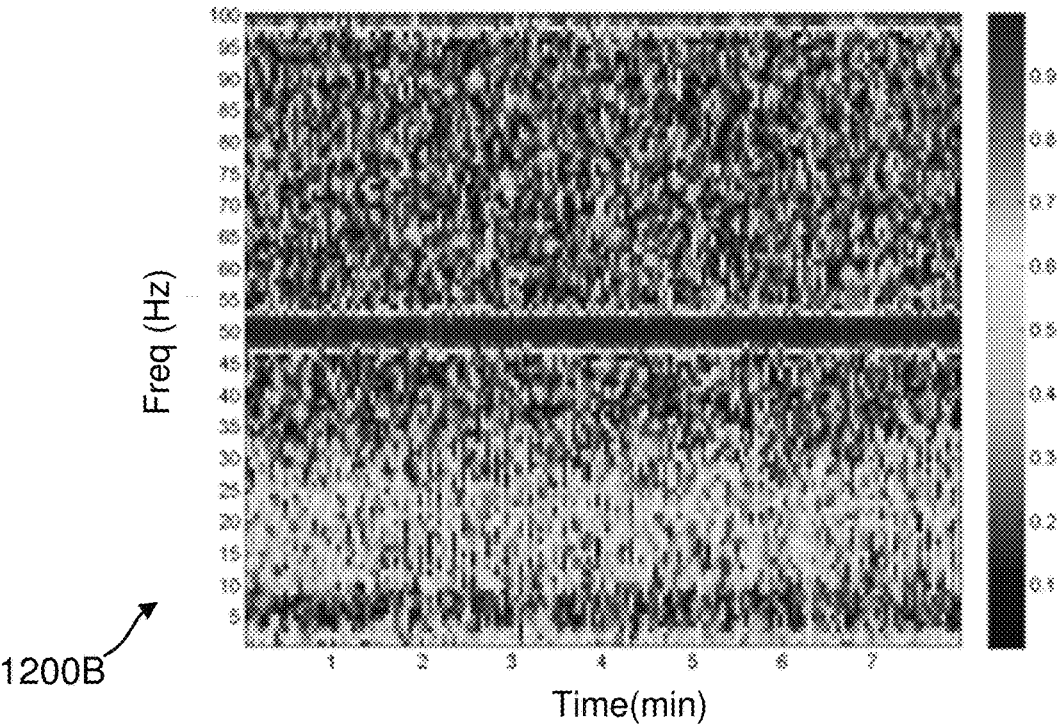
FIG. 12B

SYSTEM AND METHOD FOR CORTICAL ENTRAINMENT

CROSS-REFERENCE TO RELATED APPLICATION

This patent application claims priority under 35 USC §119(e) based on the U.S. Provisional Patent Application Ser. No. 61/734,889 filed on Dec. 7, 2012, the disclosure of which is incorporated herein in its entirety.

TECHNICAL FIELD

The present disclosure relates to methods and systems for cortical entrainment.

RELATED ART

Epilepsy is a world-wide disorder affecting millions of people of all ages and ethnic groups with substantial impact on quality of life, morbidity, and mortality. The mortality rate among people with epilepsy is typically higher than the general population, including the risk of sudden death. Epilepsy may also impose a high economic burden on society associated with health care costs that may be to the tune of billions of dollars.

Conventional treatments for epilepsy merely focus on amelioration of symptoms, but fail in effectively curing epilepsy. A large percentage of epilepsy patients continue to have seizures despite current treatments.

The most common conventional treatment is the prescription of anti-epileptic drugs, which produce vast changes in the excitation levels in a patient's central nervous system, which may lead to cognitive and behavioral deficits. In cases where medication is ineffective in controlling seizures, more invasive procedures are attempted. These include various methods of inducing brain activation such as Vagus nerve stimulation, low frequency, transcranial magnetic stimulation, deep brain/thalamic stimulation, or surgery to excise the part of the brain from where the seizures generate. In addition to the highly invasive nature of these treatments, the efficacy with which they control or terminate seizures is inconsistent and/or may only be temporarily effective.

While research increasingly focuses on the goal of curing epilepsy, finding safe, non-invasive methods of decreasing seizures, and potentially reversing the epileptogenic process will be helpful in improving the lives of those with epilepsy. Continuous efforts are being made to improve epilepsy treatments.

BRIEF DESCRIPTION OF THE DRAWINGS

The foregoing features and other features will now be described with reference to the drawings of the various embodiments. In the drawings, the same components have the same reference numerals. The illustrated embodiments are intended to illustrate, but not to limit the present disclosure. The drawings include the following Figures:

FIGS. 11-1 and 11-2 shows an example of a trio map, according to one embodiment; and FIGS. 12A-12C show examples of a patient's brain activity, according to one embodiment.

DETAILED DESCRIPTION

Figure 1:
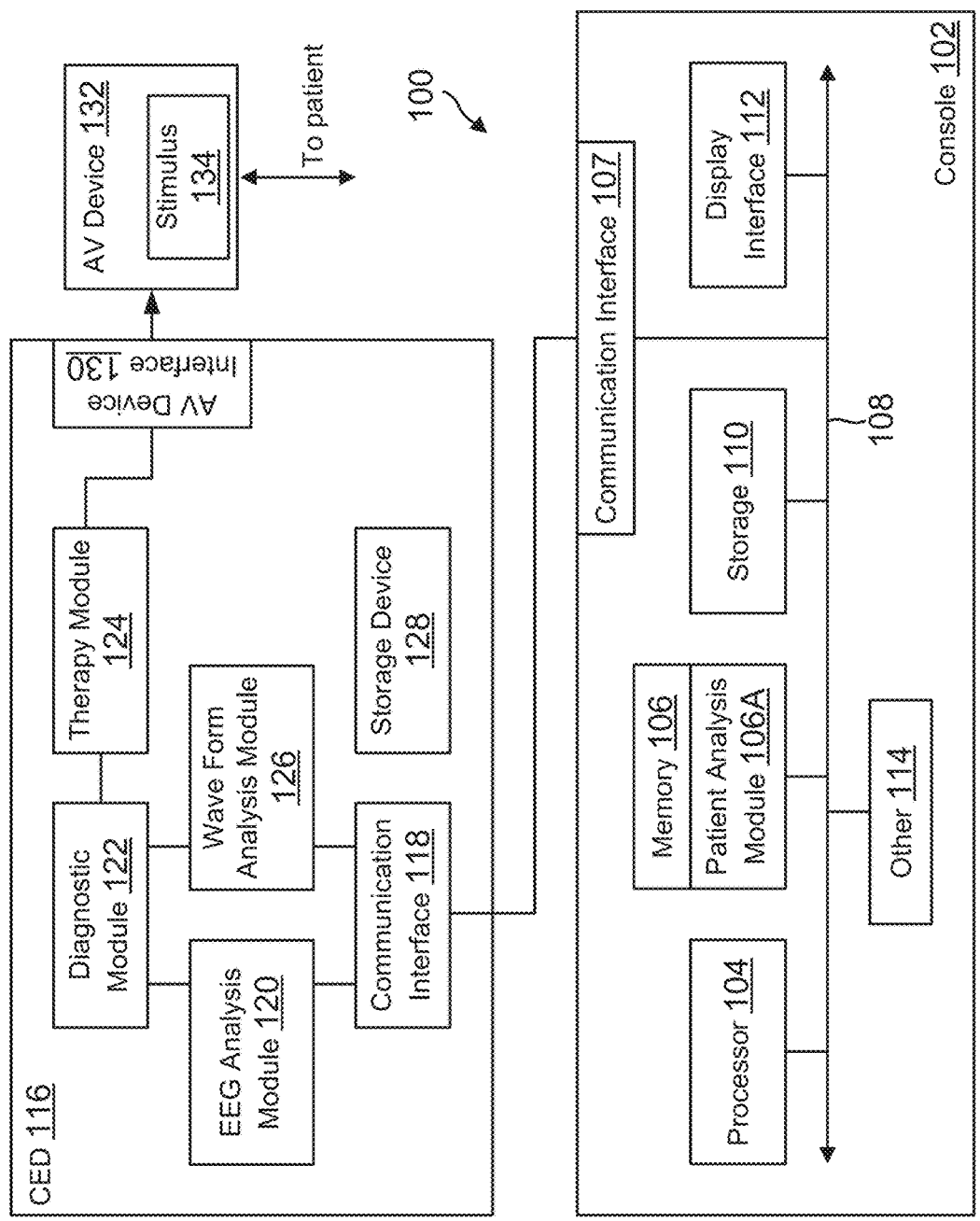
FIG. 1 illustrates a system for implementing the various embodiments of the present disclosure.

In the following detailed description of the embodiments, reference is made to the accompanying drawings in which like references indicate similar elements, and in which is shown by way of illustration specific embodiments in which the disclosure may be practiced. These embodiments are described in sufficient detail to enable those skilled in the art to practice the embodiments, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims.

As preliminary note, the terms "component", "module", "system," and the like as used herein are intended to refer to a computer-related entity, either software-executing general purpose processor, hardware, firmware, and/or a combination thereof. For example, a component may be, but is not limited to being, a process running on a processor, a processor, an object, an executable, a thread of execution, a program, and/or a computing device.

By way of illustration, both an application running on a server and the server can be a component. One or more components may reside within a process and/or thread of execution, and a component may be localized on one computing device and/or distributed between two or more computing devices. Also, these components can execute from various non-transitory, computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

Computer executable components of the present disclosure can be stored, for example, at non-transitory computer readable media including, but not limited to, an ASIC (application specific integrated circuit), CD (compact disc), DVD (digital video disk), ROM (read only memory), floppy disk, hard disk, EEPROM (electrically erasable programmable read only memory), memory stick or any other storage device, in accordance with the claimed subject matter.

In one embodiment, systems and methods for cortical entrainment are described, which incorporate diagnostic processes to customize therapeutic spectral patterns, and deliver patterns via auditory and visual stimuli to condition a brain's neural networks in a non-invasive manner. The system and methods may be used with clinical monitoring and devices to diminish and/or eliminate interictal epileptiform discharges (IEDs), and achieve improved coherence responses in electroencephalographic (EEG) waveforms.

The present disclosure provides an EEG analysis module, a waveform analysis module, a diagnostic module that classifies EEG spectrograms, a therapeutic module that correlates the EEG spectrograms and waveform characteristics with varying temporal and spectral stimuli, and a non-invasive delivery mechanism for generating prescribed visual and auditory patterns for entrainment during varying degrees of consciousness. The temporal and spectral stimuli may be isolated, or embedded in the spectral patterns of specific musical arrangements, and are uniquely encoded and maybe represented through a trion mapping model of visual and auditory patterns, which have neurophysiological significance.

In one embodiment, EEG and IED waveforms are analyzed and interpreted to assess particular patterns of brain activity, which are indicative of the various types of epilepsy and seizures, including idiopathic generalized seizures. This is achieved by comparing frequencies of oscillatory behavior synchronized between areas of the brain or within specific brain regions, and recognizing the spectral and temporal anomalies. This information is then correlated with clinically derived therapeutic protocols, as described below.

In one embodiment, initial and long-term therapies are customized from observed patient responses, and therapy is delivered during wakeful and sleep states. The therapy may include auditory and visual stimulation that has been proven to induce activity in widely distributed areas throughout the entire brain (well beyond primary auditory and visual neurological areas) and is delivered in conjunction with indirectly therapeutic content, which facilitates homeostasis. The auditory stimulus may be the primary therapy, and the visual stimulus may provide an additional stimulation pathway associated with the auditory pathway, especially if a locus of seizures falls outside the networks sufficiently affected by the auditory stimuli. The subsequently induced, normalizing patterns of brain activity may become persistent or long-lasting when presented in a prescribed sequence for an appropriate amount of exposure. With extended and repetitive use, the system and methods described herein are intended to produce alterations to the architecture of the affected, activated neural networks, and mitigate neuropathological conditions associated with epilepsy.

CED Overview:

In one embodiment, the present disclosure provides a cortical entrainment device (CED) 116 (See FIGS. 1 and 2) having an EEG analysis module 120 (FIG. 1) for processing and characterizing externally supplied EEG waveforms and a waveform analysis module 126 (FIG. 1) for processing and characterizing IED waveforms. The CED 116 may also include a diagnostic module 122 (FIG. 1) that classifies the clinical significance of the waveforms and EEG spectrograms, correlates that with potentially appropriate stimuli, and evaluates the effectiveness of therapeutic stimuli as described below in detail.

In one embodiment, the CED 116 includes a therapeutic module 124 (FIG. 1) that receives input from the diagnostic module 122 and retrieves and sequences temporal and spectral stimuli from a data structure storing therapeutic stimuli at a storage device 128 (FIG. 1). Furthermore, a non-invasive delivery mechanism 132 and 134 is provided for generating prescribed visual and auditory patterns for entrainment during varying degrees of consciousness, ranging from fully awake to deeply asleep.

In one embodiment, a patient provides input signals an EEG monitor (not shown) which is provided to the CED 116, and receives prescribed therapeutic stimuli after the signals have been processed, as described below in detail. The CED 116 may be packaged as a hearing aid, or as a handheld, mobile unit with integrated audiovisual players. The CED 116 may be a portable, fully-contained, non-implantable medical device, or it may be a portable, non-implantable medical device that prepares and conveys the visual and auditory patterns for entrainment to audiovisual players that are separate from, and remote to the device. In another embodiment, the CED 116 when used in a clinical setting, may be configured as a rack or cart mounted device in conjunction with other diagnostic equipment.

As described below in detail the CED 116 may be integrated into one unit, or separated into multiple units, based upon the packaging configurations shown in FIG. 3. The CED 116 is able to communicate with, and receive diagnostic and therapeutic updates from, a remote or a local computer running an application using standard and/or proprietary interface. In one embodiment, the CED 116 may be equipped with both a bidirectional data port and a wireless communication channel to accept bio-potential measurements from another device.

In one embodiment, the CED 116 may be configured to accept signals from a variety of EEG measurement devices, with varying data resolutions (e.g. EEG signals sampled from one or two localized electrodes, the International 10-20 electrode system, or higher resolution systems with 64 or 132 electrodes). Of course, the adaptive embodiments are not limited to any particular, device or resolution.

The EEG characterization for the CED 116 of the present disclosure may fall into two categories, namely, spectrum analyses and waveform analyses. The data from the spectral and waveform analyses is provided to the diagnostic module 122 and may be used to evaluate the therapeutic benefit of stimuli.

The diagnostic module 122, as described below in detail is used during the establishment of a therapeutic protocol, and uses real-time EEG input signals that are processed by the EEG analysis module 120, while different, and clinically representative, audiovisual stimuli are applied to a patient. Each stimulus and combination of stimuli are selected and ordered by the therapy module 124 and generated by module 226 in the CED's Mode B option, i.e. when a patient is being evaluated for a treatment plan vis-à-vis the Mode A option when a therapy plan is already in place.

Figure 6:
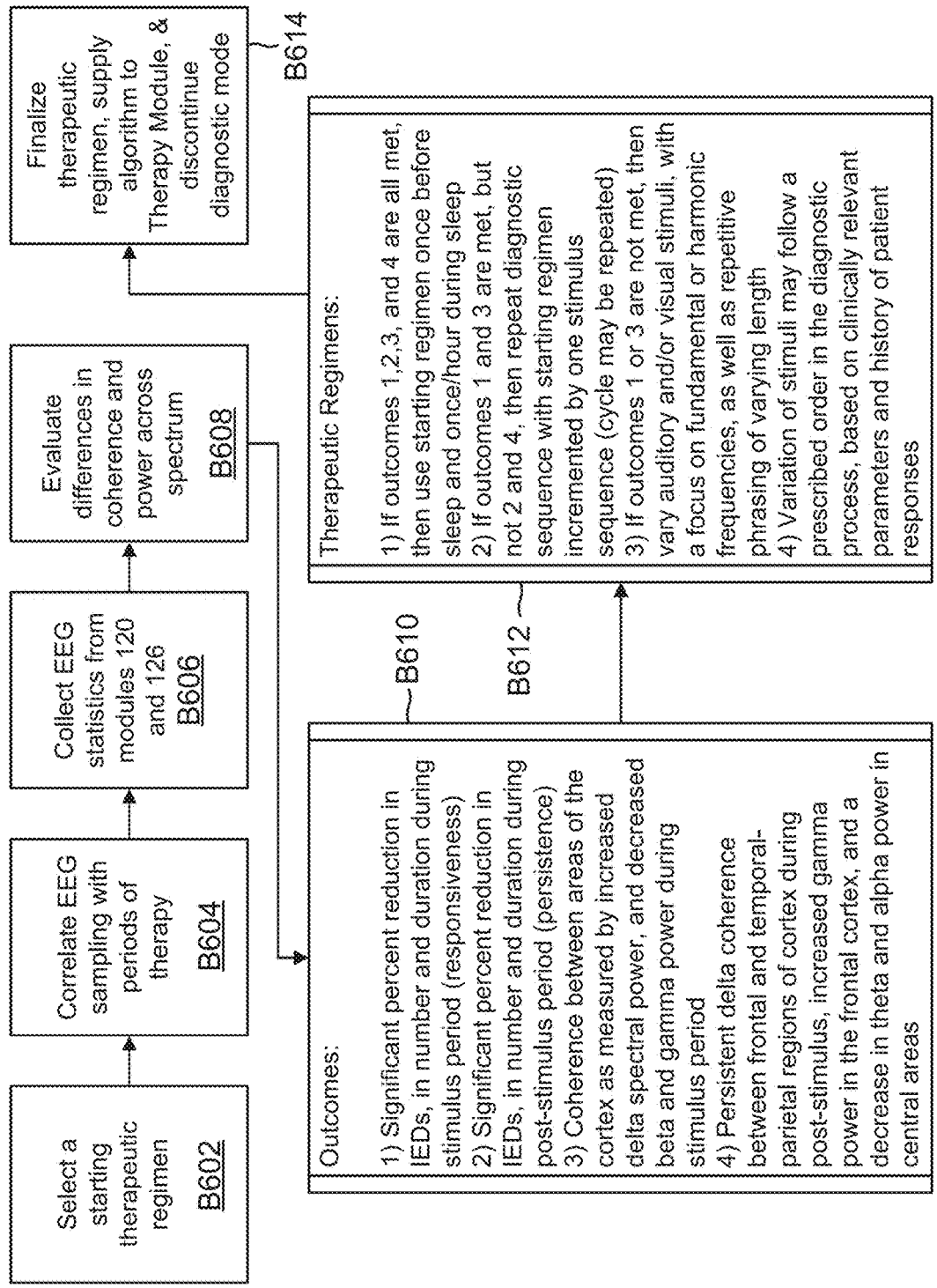

The signal processing and spectral analysis that is performed by CED 116 is compared with stored data, and the results are sorted, based on certain expected types of outcomes, shown in FIG. 6. As an example, there may be four types of outcomes: 1) A significant reduction of epileptiform activity during stimulus exposure as measured by the number and duration of IEDs, 2) A persistence in the reduction of epileptiform activity throughout a post-stimulus period as measured in the same way as for the preceding outcome; 3) The generation of significant increases in delta frequency coherence (synchronization of activity) across multiple regions of the cortex, and/or a significant decrease in alpha, beta and/or gamma coherence across the cortex during a stimulus exposure period; and 4) A persistent increase in delta coherence between the frontal and temporal-parietal cortex, a persistent increase in the amplitude and/or spectral power of gamma oscillations in the frontal region, and a decrease in theta, and alpha power spectra along the brain's central axis.

In one embodiment, as described below in detail with respect to FIGS. 7 and 8, the stimuli are applied to the patient, and EEGs are recorded for three periods that may be of equal duration (for example, 10 minutes each). These three periods correlate with a baseline therapy measurement phase (before stimulation), an active therapy measurement phase (during exposure to stimulation), and a post-therapy measurement phase (after stimulation is finished).

The spectrographic analyses are completed, and signal processing routines determine the spectral power for particular frequency bands during the baseline, active and post-therapy periods. The total delta waveform power is determined for each period (for example, 10-minute period), as measured from the brain map, as well as subsets of that brain map.

For analyzing subsets of the brain map, significant changes during different periods may also be determined by taking the baseline, dividing it into different epochs (for example, 30 epochs), and determining the mean values, and standard deviations (SD) for each point on the EEG brain map.

The CED 116 compares the mean amplitudes and SDs of the stimuli/post stimuli exposure files with those of the baseline file. The CED 116 also determines for every point the number of SDs from the mean of the baseline.

After the first diagnostic sequence (i.e. baseline period, stimulus period, and post-stimulus period), the diagnostic module 122 rates and weighs the expected outcomes based on how the measured data compares with baseline statistics and stored thresholds for the data (as shown and described below with respect to FIG. 6). Paired t-tests may be used to determine differences, and compare epileptiform discharge frequencies before, during, and after exposure to the stimuli. If the paired t-tests demonstrate statistical significance, or the reduction in baseline epileptiform discharges (IEDs) is clinically meaningful (e.g. more than 20% for one type of condition), then the therapy is considered effective, and may be prescribed.

Figure 7:
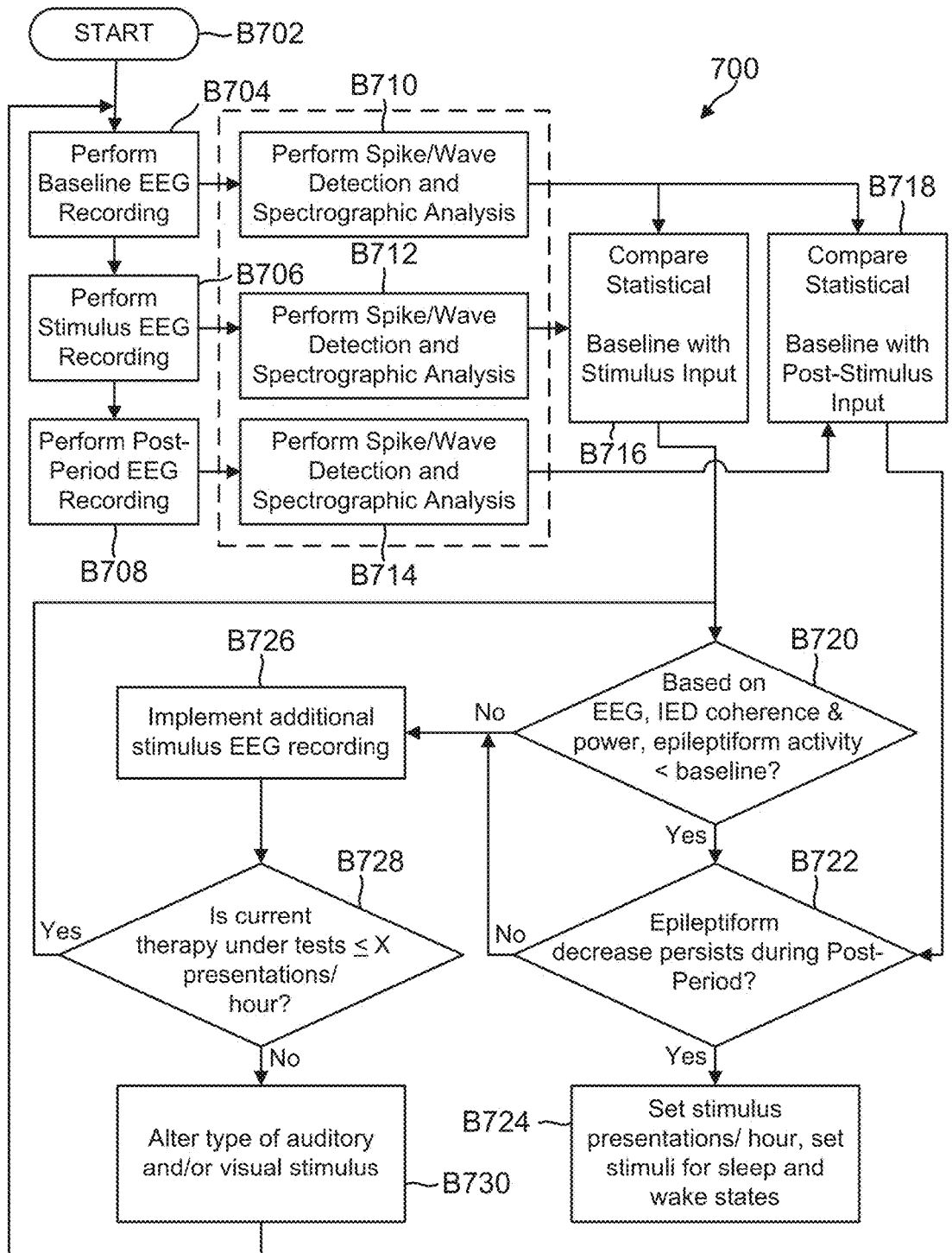
Figure 8:
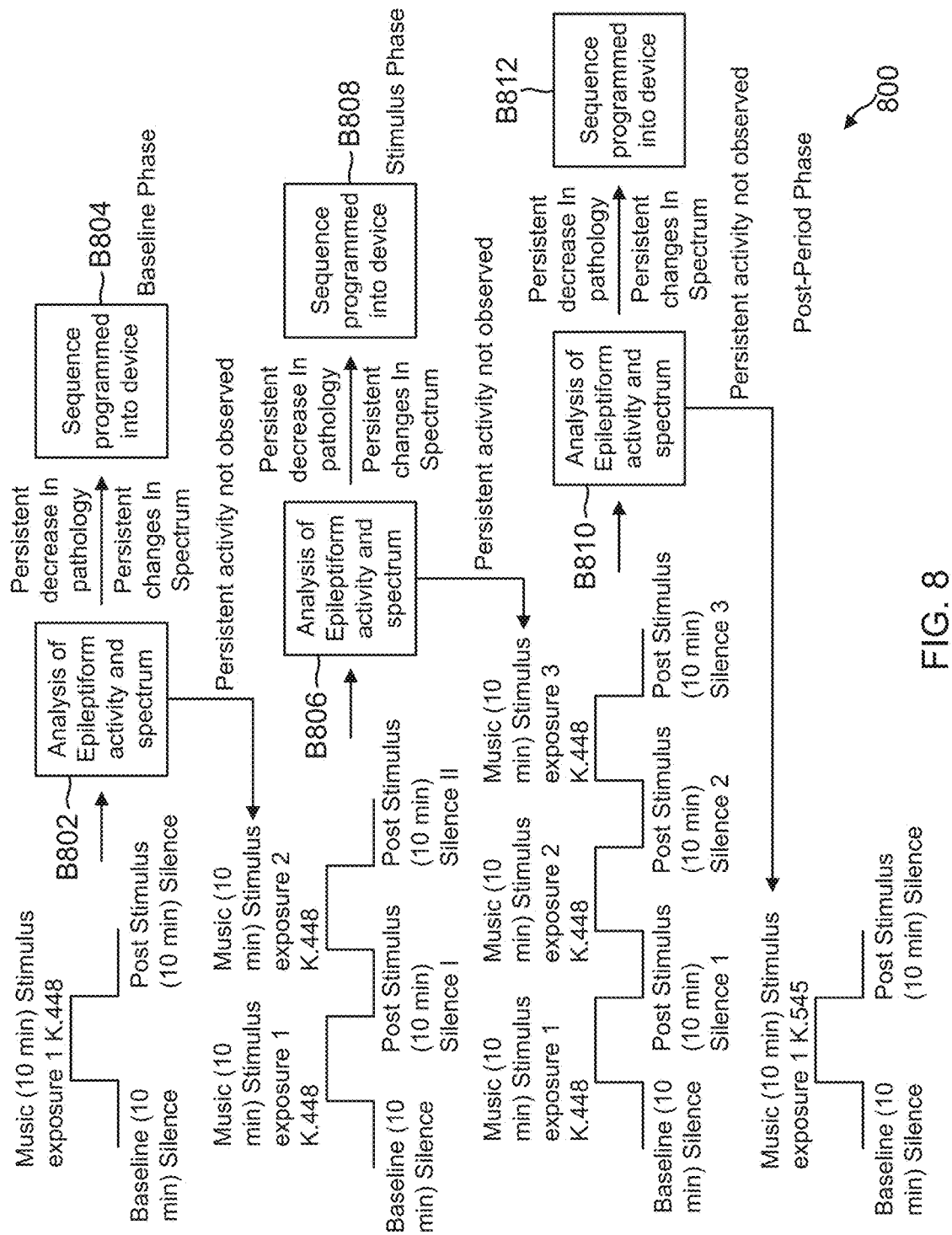

If the outcomes listed above and in FIG. 6 are all met, the diagnostic module 122 instructs the therapy module 124 to repeat the stimuli, for example, once/hour throughout all sleep states as shown in FIGS. 7 and 8 and described below in more detail. A single manual exposure may be administered prior to sleep, or at the convenience of the patient during waking.

If conditions 1 and 3 are met, but not 2 and 4 (i.e. therapeutic changes and activity pattern changes are observed during the stimuli, but are not persistent), then an additional presentation of the stimulus and post-stimulation period are added to the diagnostic sequence, and the analysis and statistical comparisons may be repeated.

If conditions 1-4 are subsequently met, the sequence with 2 repeated cycles of stimuli may be programmed into the CED 116 for presentation each hour during sleep, along with a single manual presentation of the 2-stimulus period sequence administered prior to sleep, or at the convenience of the patient during waking.

If during the second diagnostic sequence, conditions 2 and 4 are not met, then a third presentation of the stimulus and post-stimulation periods may be added to the overall presentation sequence.

If conditions 1-4 are met after the third stimulus period, then this 3-stimulus period sequence is programmed into the CED 116 for presentation each hour during sleep along with a single, 3-stimulus period sequence administered prior to sleep, or at the patient's convenience.

During the diagnostic sequences, depending upon the strength of the outcomes, the types of audiovisual stimuli may be varied, and the brain's response is evaluated. The diagnostic procedure may be repeated with auditory and visual stimuli possessing lower and higher frequency harmonics and fundamentals, and longer and shorter long-term periodicities. Pearson correlation coefficients may be used to test correlations of the effects between different stimuli so that the most effective therapy is selected.

The final therapeutic protocol may include auditory stimuli, or visual stimuli, or a combination of both. Once the diagnostic regimen is identified, the therapy module 124 is programmed to deliver the prescribed stimuli via its Mode A option. In one embodiment, during Mode A, EEG or IED waveforms may not be collected and evaluated, nor are they synchronized with the therapeutic cycles. Several different types of stimuli may be stored, including but not limited to, tonal collections, musical compositions, and video representations of mapped neural patterns, which may be programmed to achieve a specific synchronicity, temporal periodicity of repetitions, and harmonic frequency.

The therapy module 124 is given a set of operating parameters during the diagnostic mode of the CED 116, and delivers that protocol until reset by a clinician. The therapy module 124 retrieves and sequences the audio and visual components of the stimuli and provides the content to signal generators (226/228, FIG. 2). The final output may be regulated by a switch, and a sleep detector module that may be reset by the patient.

The stimuli stored by the CED 116 includes stimuli that has been clinically demonstrated to produce therapeutic effects, as well as patterned spectral and temporal stimuli that are similar, and provide clinically meaningful variations.

In one embodiment, the CED 116 may include an audio/visual player function that creates digital files from a prescribed therapeutic pattern and also has a volume control. The player is triggered to operate by the therapeutic module 124, as well as by a sleep detector switch (230, FIG. 2) that identifies whether the patient is vertical or horizontal. The therapeutic AV stimulation is provided to the patient through a variety of device interfaces (e.g. loudspeakers, portable headphones, players, displays, and hearing aids), and produces normal conversational levels of sound (e.g. adjustable 50-70 db). For stimulation that is embedded in music, the output is reproduced over one or more channels to allow for a more natural sound. Unlike audio/visual players intended for entertainment purposes, the CED 116 may not permit the user to select or download the audio and video programs on the player, or adjust the volume control to be inaudible.

In another embodiment, the CED 116 incorporates the capability to both directly connect, and wirelessly relay the prescribed stimuli to speakers, headphones, hearing aids, or external displays, and to synchronize with a physician's device-specific software either directly through the data port, or over a telecommunications interface.

System 100:

FIG. 1 is a high-level block diagram of system 100, in which executable instructions as described below can be implemented. Note that certain standard and well-known components which are not germane to the present disclosure are not shown in FIG. 1.

System 100 includes a physician's console (may simply be referred to as console) 102, CED 116 and an AV device 132, according to one embodiment. The term console as used herein includes a desktop computer, a laptop, a server, a tablet, a mobile device or any other computing device/system. The embodiments disclosed herein are not limited to any particular console type.

Console 102 may include one or more processors 104 and memory 106, coupled to a bus system 108. The bus system 108 is an abstraction that represents any one or more separate physical buses and/or point-to-point connections, connected by appropriate bridges, adapters and/or controllers. The bus system 106, therefore, may include, for example, a system bus, a Peripheral Component Interconnect (PCI) bus, a HyperTransport or industry standard architecture (ISA) bus, a small computer system interface (SCSI) bus, a universal serial bus (USB), or an Institute of Electrical and Electronics Engineers (IEEE) standard 1394 bus (sometimes referred to as "Firewire").

The processors 104 are the central processing units (CPUs) and, thus, control the overall operations of console 102. In certain embodiments, the processors 104 accomplish this by executing programmable instructions stored in memory 106, for example, patient analysis module 106A, described below in detail. A processor 104 may be, or may include, one or more programmable general-purpose or special-purpose microprocessors, digital signal processors (DSPs), programmable controllers, application specific integrated circuits (ASICs), programmable logic devices (PLDs), or the like, or a combination of such hardware based devices.

Memory 106 represents any form of random access memory (RAM), read-only memory (ROM), flash memory, or the like, or a combination of such devices. Memory 106 includes the main memory of console 102.

Also connected to the processors 104 through the bus system 108 are one or more internal mass storage devices 110. Internal mass storage devices 110 may be or may include any conventional medium for storing data in a non-volatile manner, such as one or more magnetic or optical based disks.

Console 102 includes a communication interface 107 that provides console 102 with the ability to communicate with remote devices and systems including CED 116, as described below in more detail.

Console 102 may also include a display device that interfaces with processor 104 via a display device interface 112. The display device may be used to display diagnostic results, as described below in more detail.

Console 102 may also include other devices 114, for example, one or more input/output (I/O) devices (not shown) that may include, for example, a keyboard, a mouse and others. Details of these devices are not germane to the embodiments disclosed herein.

System 100 also includes CED 116 that can communicate with console 102 via communication interface 118 and with the AV device 132 via AV device interface 130. CED 116 may use wireless, wired, network or any other connection type to communicate with AV device 132 and/or console 102. The embodiments described herein are not limited to any particular interface type or methodology.

CED 116 includes the EEG analysis module 120 (may be referred to as module 120) and the waveform analysis module 126 (may be referred to as module 126) for performing signal processing on EEG and IED waveforms. Modules 120 and 126 interface with the diagnostic module 122 that is used to establish a therapy protocol implemented by the therapy module 124, described below in detail.

AV device 132 includes a storage device 134, for example, a non-volatile memory for storing stimuli that is received from the therapy module 124. Details regarding the stimuli are provided below.

Figure 2:
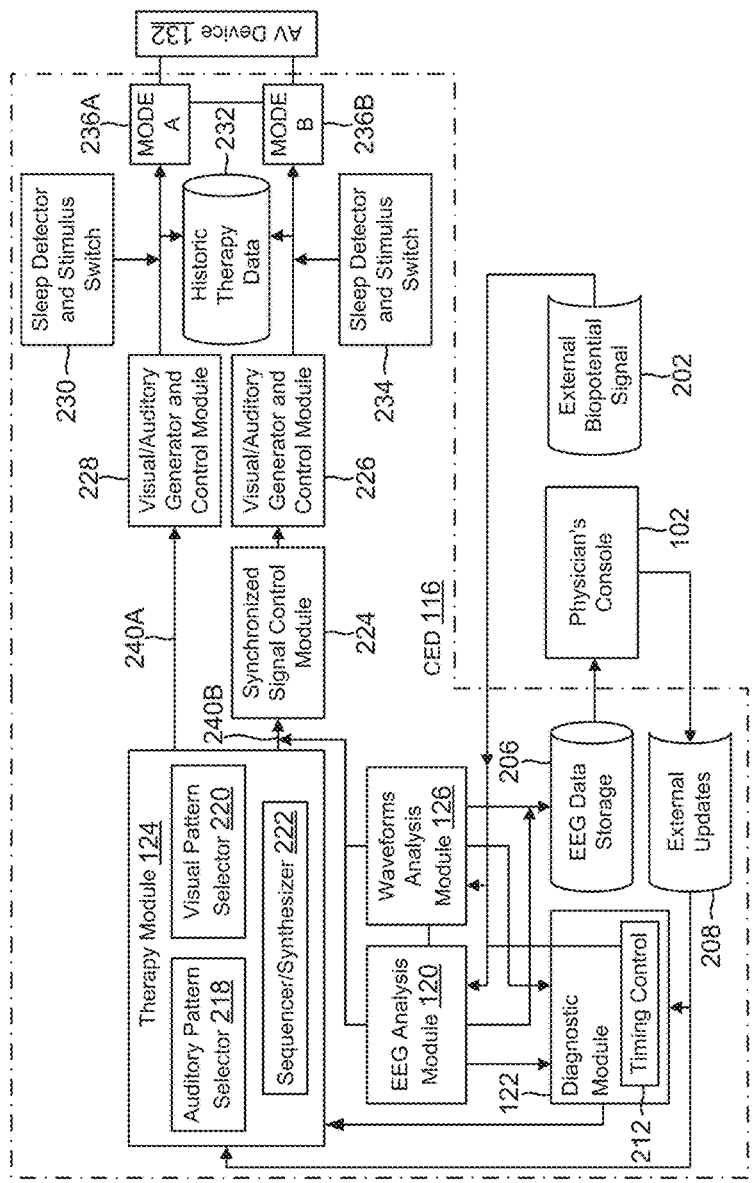
FIG. 2 shows a functional block diagram of a cortical entrainment device (CED), according to one embodiment.

FIG. 2 shows detailed functional block diagram of CED 116, according to one embodiment. It is noteworthy that the various modules and components of CED 116 may be implemented as hardware based processors, ASICs, state machines and/or software/firmware instructions. CED 116 includes a storage device 206 for storing EEG data that also may be provided to physician's console 102. CED 116 may also receive updates from the physician's console 102 that may be stored at storage device 208. The updates may be used to alter a therapy protocol, as described below in more detail. Storage devices 206 and 208, may be separate or part of a same physical storage device.

CED 116 receives biopotential signals 202 from an external device (For example, an EEG monitor). Signals 202 may be EEG waveforms that are analyzed by module 120 and module 126. Module 120 performs a spectrum analysis and the IED waveform analysis is performed by module 126.

In one embodiment, module 120 performs an EEG spectrographic analysis using a short-time Fourier transformation of digitized EEG data, for example, a 2 s-time-window moving, with 1 s overlap, pad ratio=5, and frequency resolution=0.1 Hz. Further signal processing for amplitude, absolute power and cross-power spectra are performed as a function of frequency, and are sorted into the following frequency bands/brainwaves: Delta brainwaves (Approximately 1-3.5 Hz); Theta brainwaves (Approximately 4-7.5 Hz); Alpha brainwaves (Approximately 8-12.5 Hz); Beta 1 brainwaves (Approximately 13-18 Hz); Beta 2 brainwaves (Approximately 19-25 Hz); Gamma brainwaves (Approximately >25 Hz)

The frequency bands correlate with indicators of brainwave activity, however, the CED 116 may be reprogrammed to alter band ranges, and allow for greater physiologic variation, as well as adoption of any new diagnostic protocols.

In one embodiment, module 126 performs IED waveform analysis, which may include filtering of an input (202) to separate the frequencies of major brainwaves. Each brainwave is analyzed for both a number of discharges, and a duration of sustained spikes (i.e. sharply changing polarity) and wave (sinusoidal type) complexes. As an example, this signal processing may be executed by module 126 device with a two-sample, zero-crossing detection algorithm, and a peak and trough detection algorithm.

The diagnostic module 122 receives input from modules 120 and 126. The process for using the diagnostic module 122 is described below.

The therapy module 124 receives an input from the diagnostic module 122 to provide a certain audio/video stimuli to a patient, either in Mode A (236A) (i.e. ongoing therapy) or Mode B (236B), where a baseline is being established for a patient. The therapy module 124 includes a storage device (not shown) for storing audio and visual patterns. The audio pattern is selected by the auditory pattern selector module 218 and the visual pattern selector module 220 selects the visual pattern. A sequencer/synthesizer 222 is used to sequence and synthesize an audio/visual output to the therapy module 124.

The output 240A from the therapy module 124 is for Mode A and output 240B for Mode B. In Mode A, the output is controlled by module 228 based on the sleep detector and stimulus switch 230 that detects when the patient is awake or asleep.

Output 240B for mode B is used for establishing a baseline therapy protocol. Module 224 synchronizes output 240B with the patient's EEG signal as it available through modules 126 and/or 120, and diagnostic operations are performed on the patient's response to the stimuli. The stimuli presented to the patient are based on switch 234 detection and controlled by module 226.

Stimuli that are presented to the patient may be stored as historical therapy data 232 at a storage device. This data may be made available to a physician that monitors patient therapy, as described below in detail.

Figure 3:
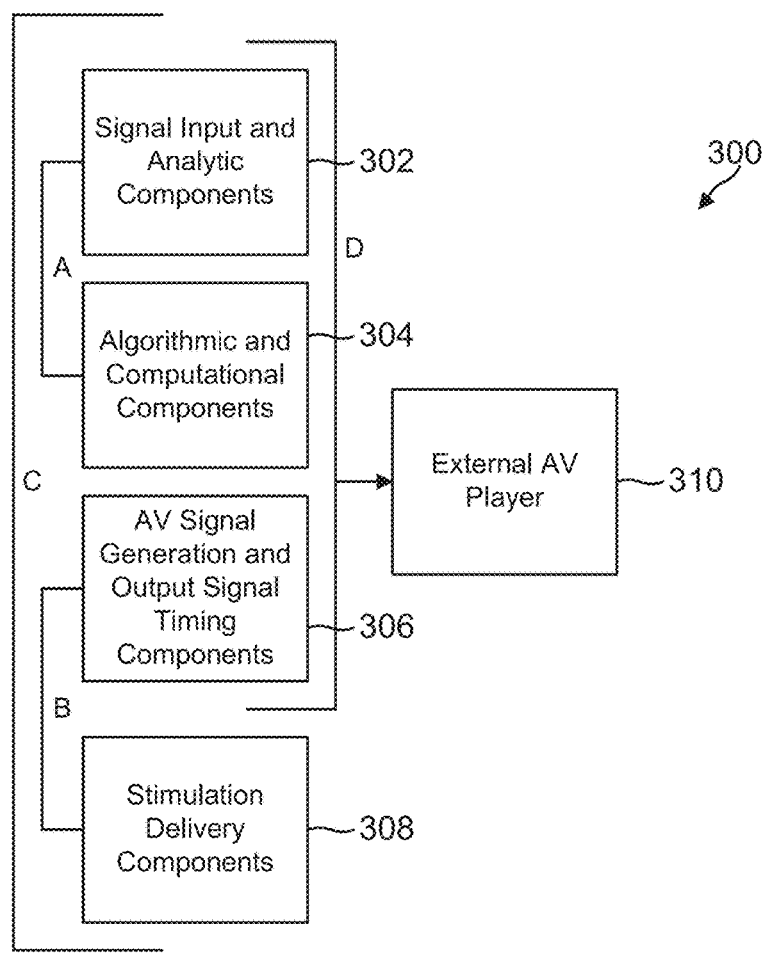
FIG. 3 shows examples of different configurations for the CED device of FIGS. 1 and 2, according to one embodiment.

FIG. 3 shows an example of various CED 116 configurations. The embodiments are not limited to these configurations and instead show examples of how CED 116 may be packaged based on user needs.

A first configuration is shown as functional configuration A with components 302 and 304. Configuration B may have components 306 and 308, while configuration C may have components 302, 304 and 306. Configuration D may have all 302, 304, 306 and 308. The various configurations may interface with an external AV player 310.

Figure 4:
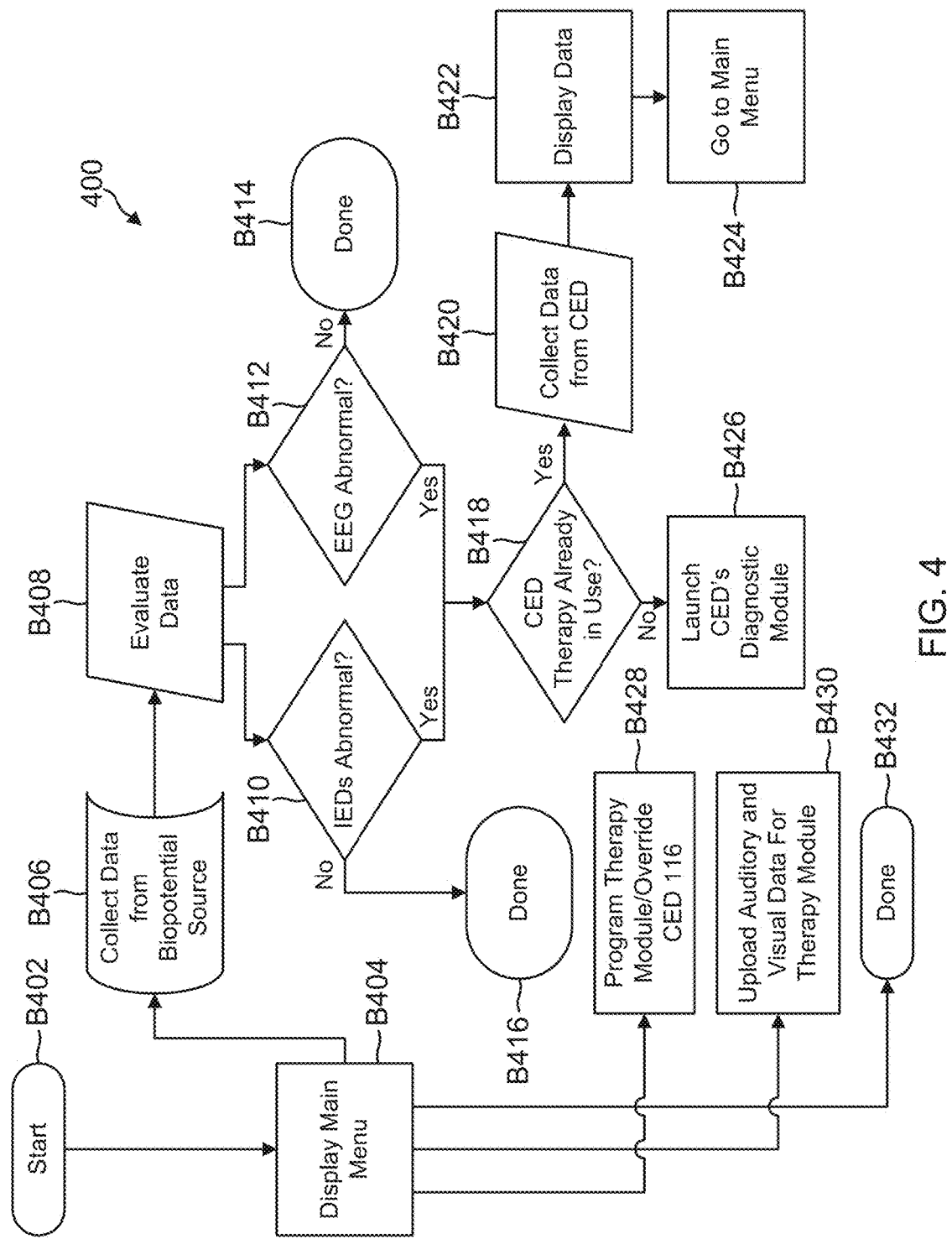
FIGS. 4-9 show various process flow diagrams; according to various embodiments of the present disclosure.

FIG. 4 shows a process 400 based on execution of module 106A by processor 104 out of memory 106, according to one embodiment. The process begins in block B402, when console 102 and CED 116 are initialized and operational. A graphical user interface (GUI) or a command line interface (CLI) is presented at a display device. In block B404, a main menu with selectable options is presented. The options may include updating information, analyzing collected data and others.

In block B406, data may be collected from a biopotential source, for example, an EEG monitor. The collected data has EEG waveform and IED components. Both the IED and EEG waveform data is evaluated in block B408. In block B410, the collected IED data is compared with historical IED data, if any. If the IED data is not abnormal (i.e. no IEDs occur within the EEG data), then the process ends in block B416, after the collected data is stored. If the collected IED is abnormal, then the process moves to block B418 that is described below.

In block B412, the collected EEG data is compared with historical EEG data. If the EEG data is not normal (e.g. if the data exhibits spike and wave complexes or abnormal spectral characteristics), then the collected data may be stored and the process ends in block B414. If the EEG data is also abnormal, then the process moves to block B418.

In block B418, the process determines if CED based therapy for the patient is already in use. If yes, then more data is collected from CED 116 in block B420. The data may be displayed at the physician's console in block B422 or made available to the physician in any other form. Thereafter, the physician may go to the main menu in block B424. The physician may alter the therapy or maintain the same therapy based on the deviation in block B410 and 412.

It is noteworthy that application 106A may also be used to program the therapy module 124 or override the CED 116 (B428). Application 106A may also be used to upload auditory and visual data for therapy module in block B430.

Figure 5:
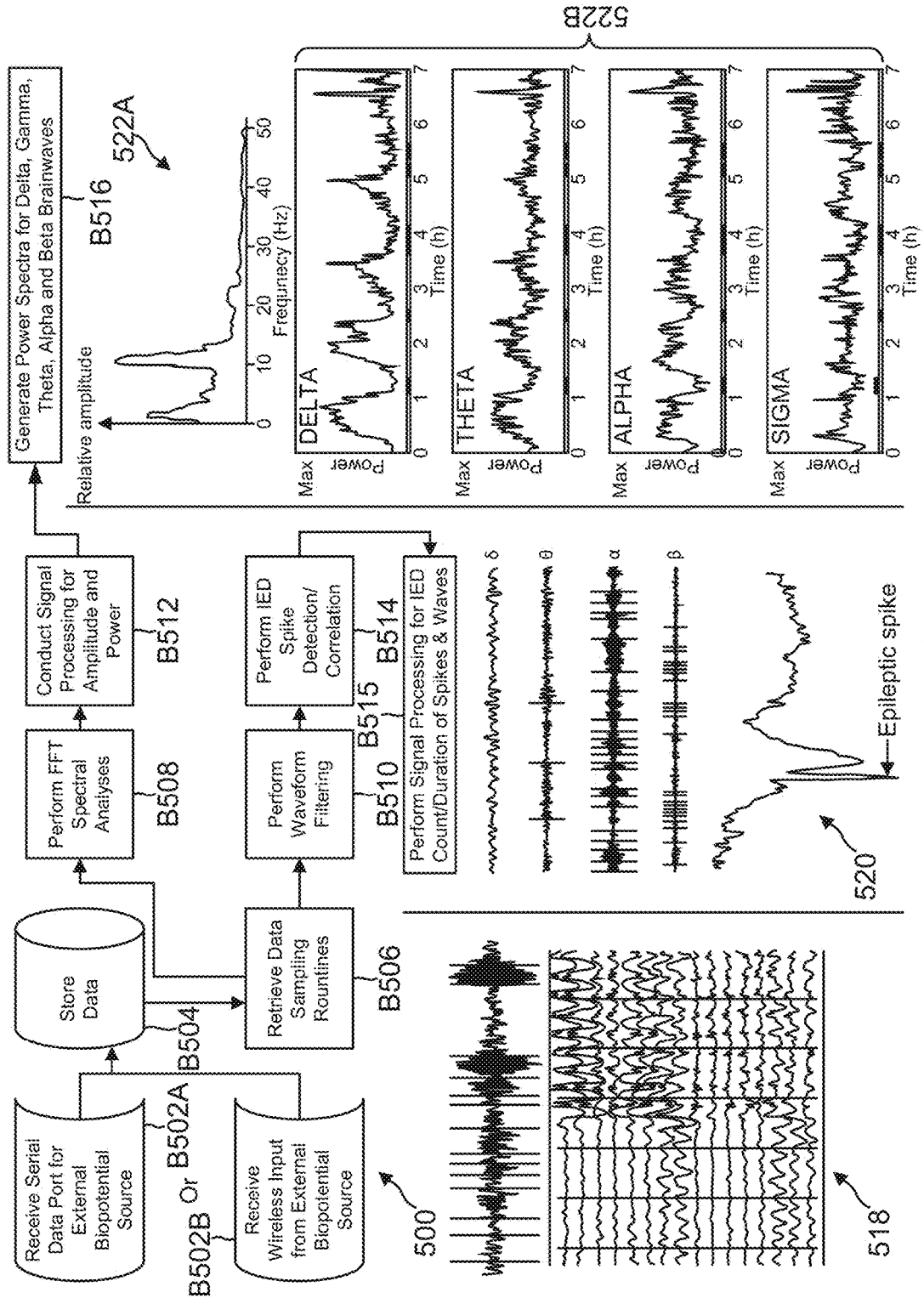

FIG. 5 shows a process 500, primarily executed by module 120 and module 126 of CED 116, according to one embodiment. The process begins in block B502A and/or B502B, when serial or wireless input is received from an external biopotential source. An example of an input signal is shown as 518. The received signal may be stored at a storage device in block B504. The stored data is then retrieved in block B506.

In block 8508, module 120 performs a FFT spectral analysis. In block B516, signal processing for amplitude and power is performed. In block B516, the power spectra for delta, gamma, theta, alpha and beta brain waves may be produced. An example of the brain waves is shown as 520 and 522B.

The waveform analysis begins in block B510, when module 126 performs waveform filtering. In block B514, IED spike detection and correlation is performed. Thereafter, signal processing for IED count and duration of spikes and waves is executed in block B515. An example of pathological IED spikes and waves is shown as 520 and 522A.

FIG. 6 shows a process 600 that is executed by one or more modules of CED 116, according to one embodiment. The process begins in block B602, when a starting therapeutic regimen for a patient with epilepsy is selected. A physician may select the starting regimen based on historical data in modules 122 and/or 124.

In block B604, the diagnostic module 122 correlates EEG sampling with different therapy durations (i.e. baseline phase, stimulus phase and post-stimulus phase durations). In block B608, EEG statistics are collected from module 126 and/or module 120. The difference in coherence and power across the wave spectrum is evaluated in block B608.

The evaluation may result in at least four outcomes that are listed in block B610 and include the following: (1) A significant reduction of epileptiform activity during stimulus exposure as measured by the number and duration of IEDs; (2) A persistence in the reduction of epileptiform activity throughout the post-stimulus period as measured in the same way as for the preceding outcome; 3) The generation of significant increases in delta frequency coherence (synchronization of activity) across multiple regions of the cortex, and/or a significant decrease in alpha, beta and/or gamma coherence across the cortex during the stimulus exposure period; and 4) A persistent increase in delta coherence between the frontal and temporal-parietal cortex, a persistent increase in the amplitude and/or spectral power of gamma oscillations in the frontal region, and a decrease in theta, and alpha power spectra along the brain's central axis.

Based on the outcomes, various therapeutic regimens may be selected from block B612. For example, if outcomes 1, 2, 3 and 4 are all met, the diagnostic module 122 instructs the therapy module 124 to repeat the stimuli, for example, once/hour throughout all sleep states as shown in FIGS. 7 and 8 and described below in more detail. A single manual exposure may be administered prior to sleep, or at the convenience of the patient during waking.

If outcomes 1 and 3 are met, but not 2 and 4 (i.e. therapeutic changes and activity pattern changes are observed during the stimuli, but are not persistent), then an additional presentation of the stimulus and post-stimulation period are added to the diagnostic sequence, and the analysis and statistical comparisons may be repeated.

If conditions 1-4 are subsequently met, the sequence with 2 repeated cycles of stimuli may be programmed into the CED 116 for presentation each hour during sleep, along with a single manual presentation of the 2-stimulus period sequence administered prior to sleep, or at the convenience of the patient during waking.

If during the second diagnostic sequence, conditions 2 and 4 are not met, then a third presentation of the stimulus and post-stimulation periods may be added to the overall presentation sequence.

If conditions 1-4 are met after the third stimulus period, then this 3-stimulus period sequence is programmed into the CED 116 for presentation each hour during sleep along with a single, 3-stimulus period sequence administered prior to sleep, or at the patient's convenience.

FIG. 7 shows an overall process 700 for conducting therapy in different phases, namely, a baseline therapy measurement phase (before stimulation), an active therapy measurement phase (during exposure to stimulation), and a post-therapy measurement phase (after stimulation is finished), according to one embodiment. The baseline phase is conducted in block B704, the stimulus phase in block B706 and the post period phase is executed in block B708. For each phase, in blocks B710, B712 and B714, respectively, modules 120 and 126 perform spike/wave detection and spectrographic analysis that has been described above.

The diagnostic module 122 compares the statistical baseline with stimulus input in blocks B716 and B718, respectively, for the baseline phase and the stimulus phase.

In block B720, the diagnostic module 122 determines if the EEG, IED coherence and power epileptiform activity is less than a baseline. If not, then in block B726, additional stimulus recording is performed. In block B728, the diagnostic module 122 determines if the current therapy under test is less than or equal to a certain number of presentations per hour, for example, 3. If yes, then the process moves back to block B720. If not, then in block B730, the auditory and/or visual stimulus is modified.

If in block B720, the EEG, IED coherence and power epileptiform activity is less than the baseline, then in block B722, the diagnostic module 122 determines if the epileptiform decrease persists during the post-stimulus phase. If not, then the process moves to block B726. Of yes, then the stimulus is set for sleep and wake states in block B724. The stimulus and the therapy program may be stored at a storage device such that a physician can retrieve the data for evaluation, as described above in detail.

FIG. 8 shows an example 800 for the process 700 described above with respect to FIG. 7. During the baseline phase, a baseline silence for a period of time (for example, 10 minutes), music stimulus (K.448) for a period of time (for example, 10 minutes), and post stimulus silence for a period of time (for example, 10 minutes) are provided. The brain activity is analyzed in block B802. If there is decrease in pathology and/or changes in the spectrum, then the applied sequence is saved in block B804.

After the baseline phase, the stimulus phase is executed in blocks B806 and B808, while the post-period phase is executed during blocks B810 and B812. The various blocks and the stimulus provided to a patient are self-explanatory.

Figure 9:
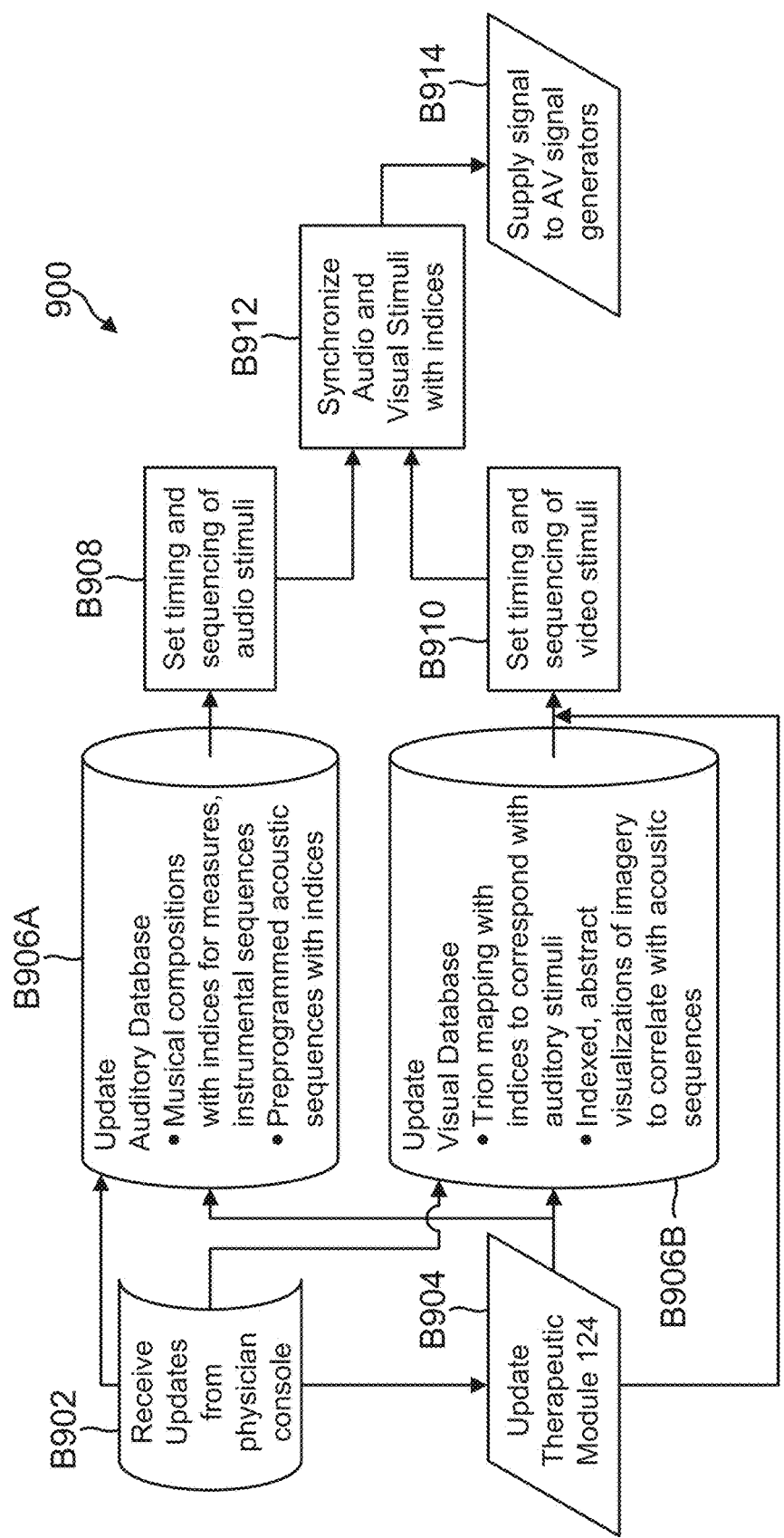

FIG. 9 shows a process 900 for providing a therapeutic stimulus to an epileptic patient, according to one embodiment. The process begins in block B902, when updates for stimulus are received from console 102 or from diagnostic module 122. The therapy module 124 data structures are updated in block B904, based on the received updates. The auditory database (at module 218) is updated in block B906A, while the visual database (at module 220) is updated in block B906B. Thereafter, the timing and sequence for audio stimuli are set in block B908, while the video (or visual) stimuli are set in block B910. The signals are synchronized in block B912 and the synchronized signals are supplied to an AV signal generator (for example, device 132 or 228). Thereafter, the process ends. It is noteworthy that the stimuli stored by the CED 116 may include stimuli that have been clinically demonstrated to produce therapeutic effects, as well as patterned spectral and temporal stimuli that are similar, and provide clinically meaningful variations.

Figure 10:
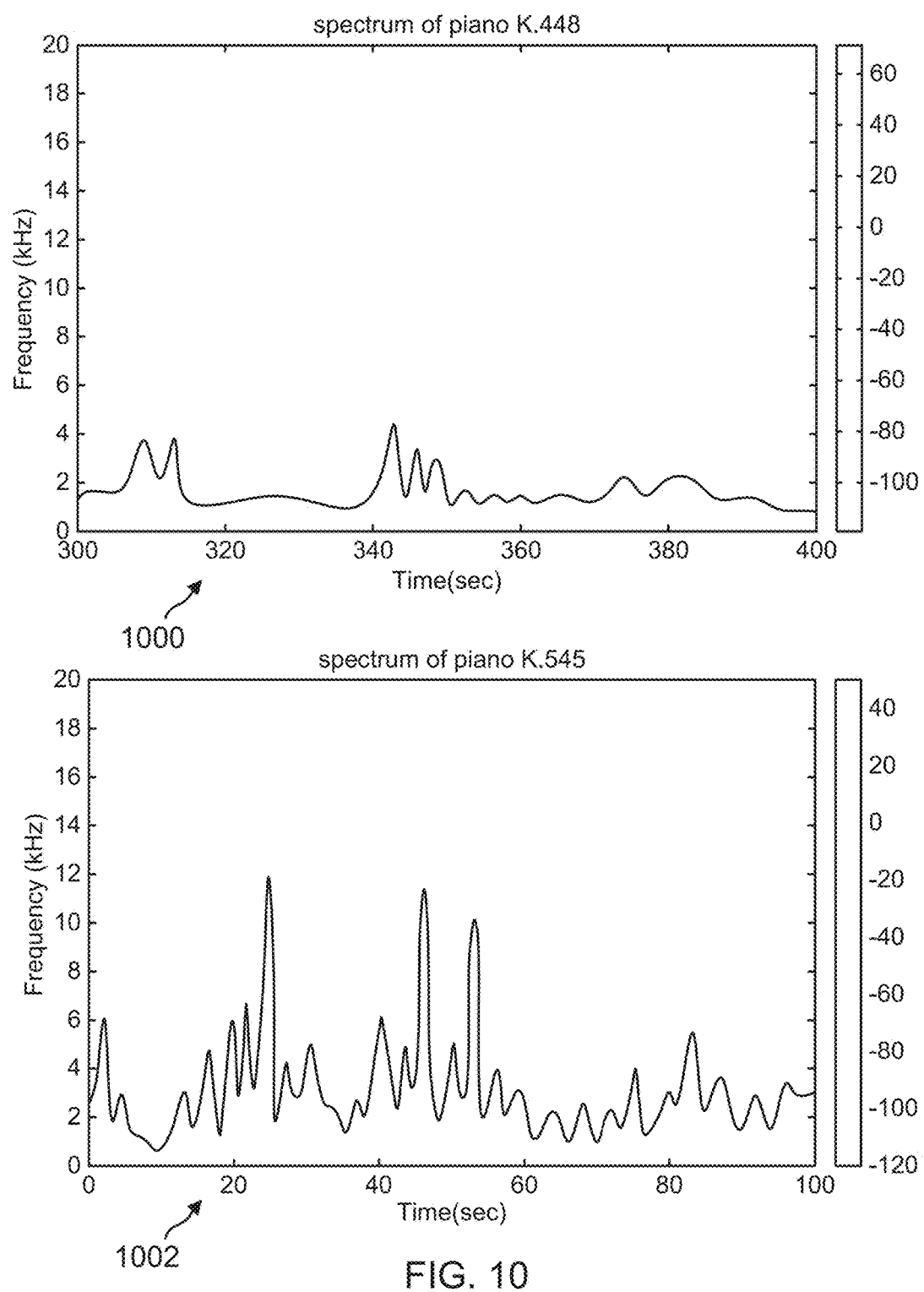
FIG. 10 shows an example of a spectrum of different music stimuli, according to one embodiment.

In one embodiment, the auditory stimuli includes a long-term periodicity of sound (for example, for 20-60 seconds), combined with a spectral emphasis concentrated in the fundamental frequency and low frequency harmonics. The auditory spectral patterns for the stimuli may also be embedded in music. For example, the CED 116 may use auditory and visual stimuli from Mozart's Sonata for Two Pianos in D Major (K.448), Mozart's piano sonata in C major (K.545), Mozart's piano sonata in E-flat major (K.282) and the third and fourth minuets of Mozart's 16 minuets for orchestra (K.176). An example of the audio stimuli is shown in FIG. 10 as 1000 and 1002. These musical compositions may be used in whole, or in part, as well as interleaved with one another, or with other prescribed auditory and/or visual stimuli.

In one embodiment, the CED 116 employs a method for characterizing auditory stimuli, which describes complex spectral and temporal characteristics. Unlike other methods that are used to classify recorded sounds (especially music) by acoustic fingerprints or spectrum analyzers, the CED's method associates acoustic patterns with functional brain mapping. This method, based on trion model, is used to classify and manage both the auditory and visual stimuli that the CED 116 delivers to the patient.

The trion model is a graphical mapping method for both mirroring an auditory stimuli and characterizing the anticipated, responsive cortical activity to the stimuli with one set of symbols. (Shaw, G L; Silverman, D J; Pearson, J C (1985). "Model of cortical organization embodying a basis for a theory of information processing and memory recall." *Proceedings of the National Academy of Sciences of the United States of America* 82 (8): 2364-8. doi:10.1073/pnas.82.8.2364). Though the theory behind the overall trion model is complex, and is correlated with the firing levels of neurons that contribute to pattern recognition, memory and learning, the visual representation used by the model with rows of tri-colored squares that form repetitive patterns, may be understood at an intuitive level. Thus in one embodiment, the CED 116 uses the trion model to provide a visual stimulus that may either reinforce the auditory stimulus or be used in place of it.

In one embodiment, the trion mapping model provides still images or an animated movie file that is synchronized with auditory stimuli. As such, recurring temporal patterns of the stimuli become clearly evident. In the CED 116, the moving, visual trion stimuli are synchronized with the auditory stimuli by a sequencer (222, FIG. 2) in the therapy module. Examples of a trion map that can be used by the embodiments herein are shown in FIGS. 11-1/11-2 as 1102, 1104, 1106 and 1108.

Figure 12C:
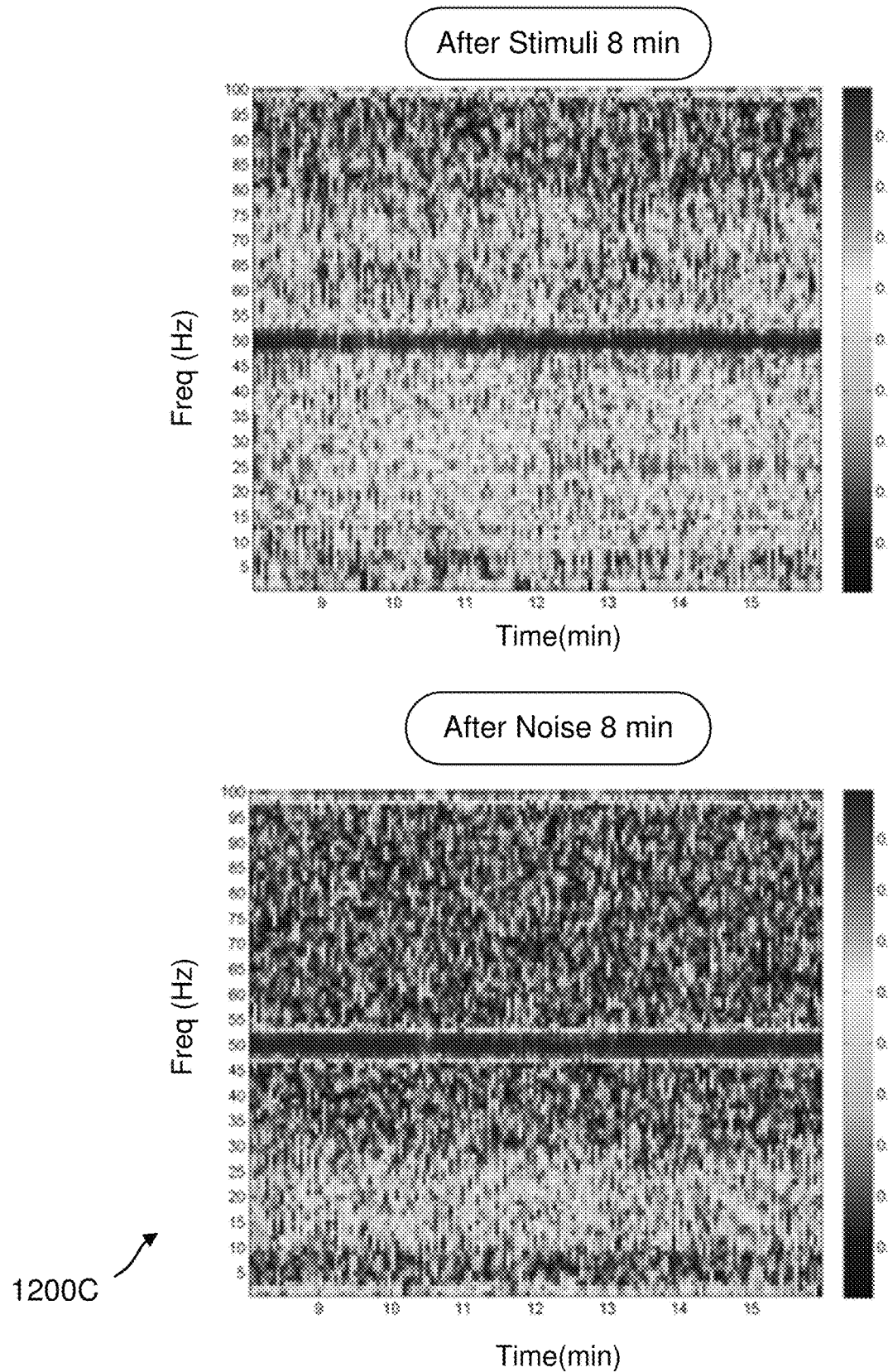

FIGS. 12A-12C show examples 1200A-1200C of brain activity of a patient before stimuli is provided, during stimuli and after stimuli, according to one embodiment.

Thus, methods and systems for cortical entrainment have been described. Note that references throughout this specification to "one embodiment" or "an embodiment" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics being referred to may be combined as suitable in one or more embodiments of the disclosure, as will be recognized by those of ordinary skill in the art.

While the present disclosure is described above with respect to what is currently considered its preferred embodiments, it is to be understood that the disclosure is not limited to that described above. To the contrary, the disclosure is intended to cover various modifications and equivalent arrangements within the spirit and scope of the appended claims.

What is claimed is:

1. A method implemented by a hardware based, cortical entrainment device (CED), comprising:

generating a power spectra with delta, theta, alpha, beta and gamma brain waves of a patient with epilepsy or a seizure disorder using an electroencephalographic (EEG) waveform;

detecting changes in interictal epileptiform discharges (IEDs) occurrence by comparing the EEG waveform with stored EEG data at a memory device of the CED; and using changes in spectral characteristic of the EEG waveform and occurrence and frequency of IEDs in the EEG waveform for providing one or both of an audio and visual stimulus for the patient from an audio/video device during a baseline phase, a stimulus phase and a post-stimulus phase of a patient therapy regimen;

wherein the baseline phase, the stimulus phase and the post-stimulus phase are conducted with different sequences, where each sequence has periods of silence and periods of stimulus that are varied based on change in the power spectra and the IEDs evaluated by the CED after each of the baseline phase, the stimulus phase and the post-stimulus phase.

2. The method of claim 1, wherein the CED interfaces with a physician console and the audio and visual stimuli stored at the CED are updated based on instructions from the physician console.

3. The method of claim 1, wherein the CED includes an auditory pattern selector module for selecting audio stimulus for the patient therapy regimen.

4. The method of claim 1, wherein the CED includes a visual pattern selector module for selecting visual stimulus for the patient therapy regimen.

5. A non-transitory machine-readable storage medium having stored thereon instructions for performing a method, comprising machine executable code, which when executed by at least a hardware based, cortical entrainment device (CED), causes the device to:

generate a power spectra with delta, theta, alpha, beta and gamma brain waves of a patient with epilepsy or a seizure disorder using an electroencephalographic (EEG) waveform;

detect changes in interictal epileptiform discharges (IEDs) occurrence by comparing the EEG waveform with stored EEG data at a memory device of the CED; and use changes in spectral characteristic of the EEG waveform and occurrence and frequency of IEDs in the EEG waveform for providing one or both of an audio and visual stimulus for the patient from an audio/video device during a baseline phase, a stimulus phase and a post-stimulus phase of a patient therapy regimen;

wherein the baseline phase, the stimulus phase and the post-stimulus phase are conducted with different sequences, where each sequence has periods of silence and periods of stimulus that are varied based on change in the power spectra and the IEDs evaluated by the CED after each of the baseline phase, the stimulus phase and the post-stimulus phase.

6. The non-transitory storage medium of claim 5, wherein the CED interfaces with a physician console and the audio and visual stimuli stored at the CED are updated based on instructions from the physician console.

7. The non-transitory storage medium of claim 5, wherein the CED includes an auditory pattern selector module for selecting audio stimulus for the patient therapy regimen.

8. The non-transitory storage medium of claim 5, wherein the CED includes a visual pattern selector module for selecting visual stimulus for the patient therapy regimen.

* * * * *